United States Patent [19]

Malek

[11] Patent Number: 4,622,011

[45] Date of Patent: Nov. 11, 1986

[54] RADICULAR POST HEAD COMPRISING REVERSIBLE RETENTION AND AUTOMATIC POSITIONING MEANS

[76] Inventor: Pierre Malek, 62, boulevard Gambetta, 06000 Nice, France

[21] Appl. No.: 643,617

[22] PCT Filed: Dec. 20, 1983

[86] PCT No.: PCT/FR83/00260

§ 371 Date: Aug. 17, 1984

§ 102(e) Date: Aug. 17, 1984

[87] PCT Pub. No.: WO84/02463

PCT Pub. Date: Jul. 5, 1984

[30] Foreign Application Priority Data

Dec. 29, 1982 [FR] France .................. 82 22203

[51] Int. Cl.$^4$ ............................................. A61C 5/08
[52] U.S. Cl. ............................... 433/221; 433/214
[58] Field of Search ............... 433/221, 220, 74, 214, 433/223

[56] References Cited

U.S. PATENT DOCUMENTS

| | | |
|---|---|---|
| 732,922 | 7/1903 | Clark .................. 433/221 |
| 1,228,488 | 6/1917 | Shaw .................. 433/221 |
| 1,397,067 | 11/1921 | Williams .................. 433/221 |
| 2,705,837 | 4/1955 | Gerlach .................. 433/221 |
| 3,255,992 | 6/1966 | Kersten .................. 433/74 |
| 3,518,761 | 7/1970 | Susman et al. .................. 433/74 |
| 3,656,236 | 4/1972 | Kurer .................. 433/221 |
| 4,334,865 | 6/1982 | Borle .................. 433/221 |
| 4,348,182 | 9/1982 | Shirota .................. 433/221 |
| 4,443,192 | 4/1984 | Blitz .................. 433/74 |

FOREIGN PATENT DOCUMENTS

| | | | |
|---|---|---|---|
| 1463860 | 12/1966 | France | .................. 433/221 |
| 1538440 | 9/1968 | France | .................. 433/221 |
| 340310 | 9/1959 | Switzerland | .................. 433/221 |

*Primary Examiner*—John J. Wilson
*Attorney, Agent, or Firm*—Dowell & Dowell

[57] ABSTRACT

A radicular post cooperating with a resilient dental impression for use in preparing a cap to be fixed to a tooth having a post hole shaped to receive the post, each post having a conical part for entering the post hole and having a cylindrical part aligned on the longitudinal axis of the post and extending from the tooth when the post is seated in the post hole, the cylindrical parts of the posts having retention grooves circularly disposed around them, the parts of the posts being fully symmetrical about the axis; and the impression being formed of a cured resilient compound having a molded hole fitting the cylindrical part of each post, and the impression holes having resilient rings shaped to enter and fill the grooves in associated posts, the shapes of the grooves and rings and the resilience of the impression compound being selected such that the cylindrical parts of the posts can be removed from and re-positioned within the holes in the impressions without damaging the impressions and while achieving accurate positioning of the posts therein because the parts of the posts are symmetrical about their axes.

2 Claims, 12 Drawing Figures

RADICULAR POST HEAD COMPRISING REVERSIBLE RETENTION AND AUTOMATIC POSITIONING MEANS

FIELD OF THE INVENTION

The invention described herein is a radicular post with a self-positioning head including a means for light and gentle retention that does not damage the dental impression. The invention concerns, in particular, the fact that the same means serves both for light retention and for self-positioning of the head of the radicular post in the impression immediately after insertion in the prepared hole.

BACKGROUND OF INVENTION AND RELATED ART

At the present time, the majority of the heads of existing radicular posts or dowels are equipped with a retentive element designed to be as effective as possible. Indeed, when an impression is to be taken of the mouth, and once the root has been prepared and the intraradicular post has been put in place, these retentive elements must maintain the radicular posts in place in the impression or negative and thereby permit withdrawal of the latter from the mouth. However, even if the radicular posts remain in the impression and are thus freed from their root, there is always the possibility that this technical withdrawal maneuver will have caused slight displacement of said posts. Moreover, posts frequently remain stuck in place when impressions are taken in the mouth. This results from the fact that the intraradicular portion of the post in the tooth root offers a large contact surface and thus creates a strong retentive force whereas the contact surface of the head of the post in the impression is relatively small.

In order to facilitate post withdrawal when impressions are taken in the mouth, post manufacturers have equipped the heads of their radicular posts with highly effective retention elements. The resulting flattened heads, ribbed heads, slotted heads and flanged heads are all designed to form a true means of anchorage in the impression compound (so called; i.e., "impression composition" (lit., "dental paste")). If, by accident, the head of a radicular post of one of these existing designs fails to lift out when an impression is taken in the mouth, it is virtually impossible to replace said head in the impression.

Due to [sic] the shape of its head (flattened, ribbed, flanged), the post lies at an angle with respect to its longitudinal axis. It is therefore impossible to determine the position the ribs or flanges were in. Furthermore, the impression compound will have been partially torn away at this point. Prior to taking an impression, numerous practitioners therefore place an index marker on the compound or on the radicular post itself in order to be able to redetermine the correct orientation should the post not lift out from the patient's mouth. Post supports or prefabricated transfer elements have also been described: these are supplementary parts designed to automatically fasten the post during impression taking, to provide precise indication of post position during manipulations thanks to index markings, to eliminate any error in post positioning, and/or to hold the post in place while the impression is taken. In practice, these additional parts [may] consist of a metal spring or slotted tube that fits onto the head of the post (see patent No. FR 1 463 860 NARBONI).

SUMMARY OF THE INVENTION

The invention eliminates all of these drawbacks. The head of the radicular post features a means of light retention that does not damage the impression and allows self-positioning of the head of the post in its housing (i.e., lit., "the cavity serving as a receptacle") in the impression. For this purpose, the head of the radicular post includes a least one continuous uniform circular groove. The number of grooves, as well as the shape of the walls or sides and/or the bottom of the grooves, are a function of the characteristics of the impression compound utilized. The circular groove must penetrate the impression compound in which it forms a ring of compound that serves as a clip and locks the head of the post in place in the impression. This locking is reversible, due to the fact of the continuity [sic] of the uniform circular groove, and due to the fact that the radicular post head is not oriented at an angle to the longitudinal axis. The shape of the groove can vary as a function of the technical characteristics of the impression compound used; the bottom of the groove may thus be either flat or cup-shaped. Likewise, the sides of the groove can form different angles with the bottom of the groove, ranging from 90° to over 130°. In addition, the angles of the sides or walls are not necessarily identical, i.e. the angle formed by the groove bottom and the side closest to the top of the head may differ from the angle formed by the groove bottom and the side closest to the intraradicular end of the post.

The top of the head of the radicular post may be conical, pan-shaped (in the shape of a truncated cone), round, rounded, spherical, hemispherical or flat. A preferred embodiment of the invention comprises a radicular post with a pan-shaped (or similar truncated) head: this shape allows the ejection or escape of serous fluids and mucus along the sides. Furthermore, thanks to the angles selected, a head with this shape top can form a prepositioned housing with the impression of the sides of the groove (which sides are parallel) that facilitates the automatic positioning or replacement of the head of the post in the impression.

The accompanying figures, which are provided solely as examples and are not exhaustive, make the invention easy to understand; these figures show a [sic] preferred embodiment of the invention.

DESCRIPTION OF PREFERRED EMBODIMENTS

Figure 1:
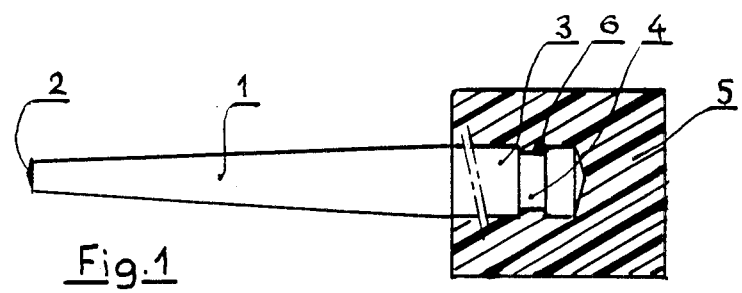
FIG. 1 is a diagrammatic side view of the radicular post in place in the impression compound, with a sectional view of the housing.

The radicular post is inserted in the tooth root by the conical part (1), which is terminated by the intraradicular tip (2) of the post.

The cylindrical part of the radicular post, which forms the head (3), is equipped with a groove or slot (4); this groove (4) constitutes a means of gentle retention which allows the impression compound (5) to serve as a clip by forming a ring (6) of compound in the groove or slot (4).

When an impression is taken, it is thus easy to understand why there is no problem even if the post or posts do not lift out with the impression or the negative provided that posts of the design subject of the present invention are used.

The user need only recover the post or posts, without worrying about their orientation and without fitting them with an index marker. The user need only insert the post in the corresponding prepared hole (8) in the impression taken of the mouth and push it in until he feels a click signifying that the post is correctly in place.

Figure 3:
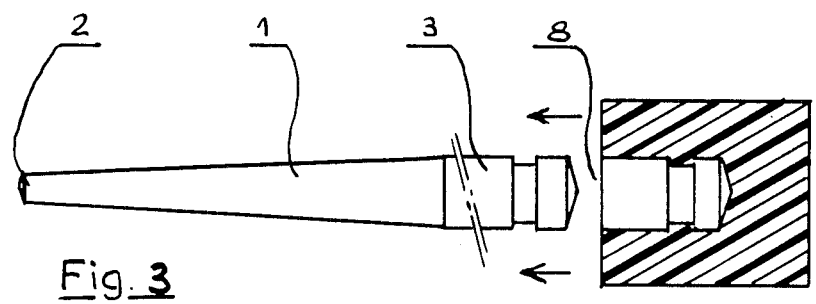
FIG. 3 is a diagrammatic side view of the radicular post after removal from the hole prepared in the impression compound.
Figure 4:
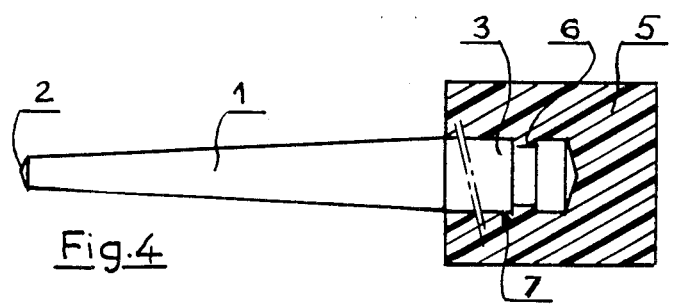
FIG. 4 is a diagrammatic side view of the radicular post in place in the impression compound, with a sectional view of the housing. This view reveals that post insertion and removal do not deform the impression compound.
Figure 5:
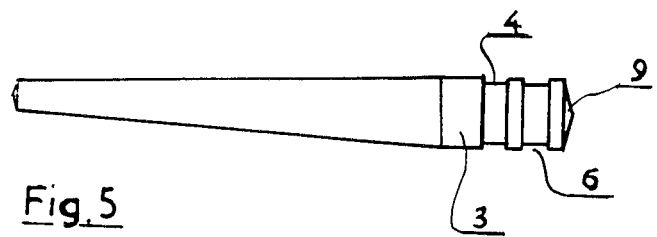
FIG. 5 is a side view of the radicular post with two grooves or slots.
Figure 6:
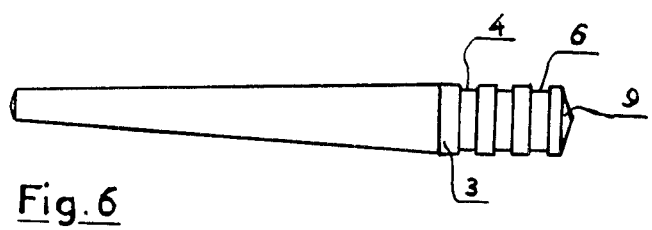
FIG. 6 is a side view of the radicular post with three grooves or slots.
Figure 7:
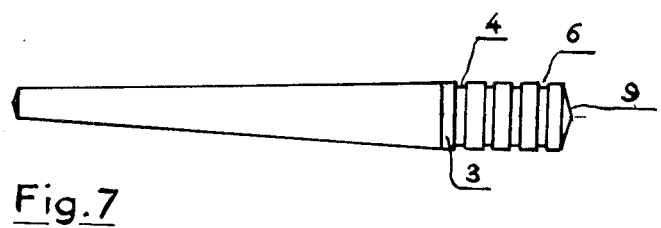
FIG. 7 is a side view of the radicular post with four grooves or slots.
Figure 8:
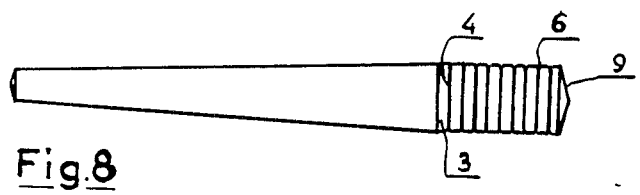
FIG. 8 is a side view of the radicular post with ten grooves or slots.

As can be seen from FIG. 3, the fact that the post remained in place in the tooth root did not deteriorate the impression compound (5).

Figure 2:
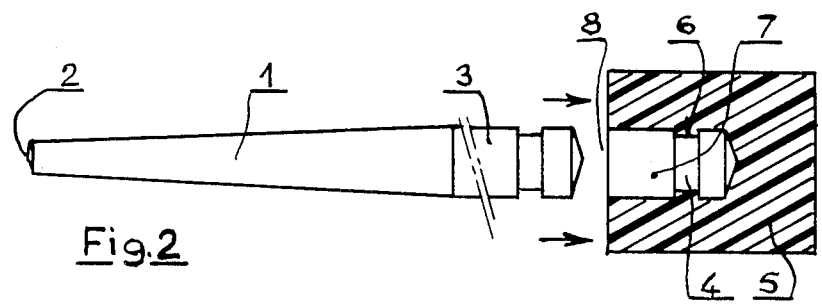
FIG. 2 is a diagrammatic side view of the radicular post in place opposite the impression compound, with a sectional view of the housing prior to insertion in the hole prepared in the impression compound.

The head (3) of the radicular post features a means for gentle retention: it does not remove any of the impression compound (5) when it (the post) is removed from its housing (7) and does not damage the impression, as occurs with posts of existing design. Furthermore, the unit is self-positioning; as shown by FIG. 2, it suffices to introduce the radicular post into its prepared hole (8) by the head (3) and to push it in until a click is felt. Due to the shape of the head (3) of the radicular post, the user does not have to worry about the angular orientation of the post with respect to its housing (7) or about the depth of insertion in the housing (7); thanks to the presence of one or more grooves, the user knows whether or not the post is correctly in place in its housing (7).

All of the above is impossible with posts of existing design which have a highly retentive head which can damage the impression compound; furthermore, the presence of the retentive elements (ribs or their counterparts) means that the head is asymmetrical, and must be fitted with an index marker or marked itself to indicate the correct position.

The post as designed by the invention thus eliminates all risks of error in positioning and in replacement, without damage to the impression, during all of the technical maneuvers required both in the dental laboratory and when the impression is taken in the mouth.

FIGS. 5, 6, 7 and 8 show heads (3) of radicular posts equipped with two or more continuous uniform circular grooves (4) which form rings of compound (6) that serves as clips. All of these post heads have the same technical characteristics: the presence of one or more grooves (4) depending on the impression compound utilized, since some such compounds are more flexible.

Figure 9:
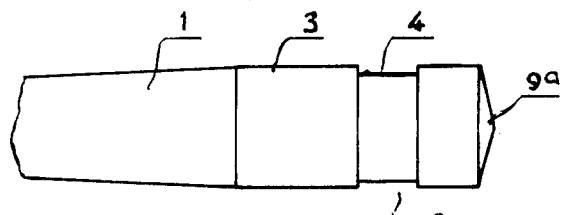
FIG. 9 is a close-up side view of the top of the head of the radicular post, which is conical.
Figure 10:
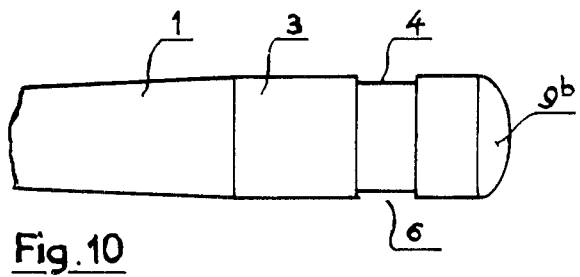
FIG. 10 is a close-up side view of the top of the head of the radicular post, which is rounded.
Figure 11:
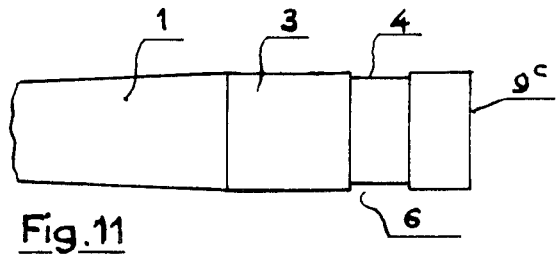
FIG. 11 is a close-up side view of the top of the head of the radicular post, which is flat.

FIGS. 9, 10 and 11 show the tops (9) of heads of radicular posts. Top (9a) is conical, top (9b) is rounded and top (9c) is flat.

Figure 12:
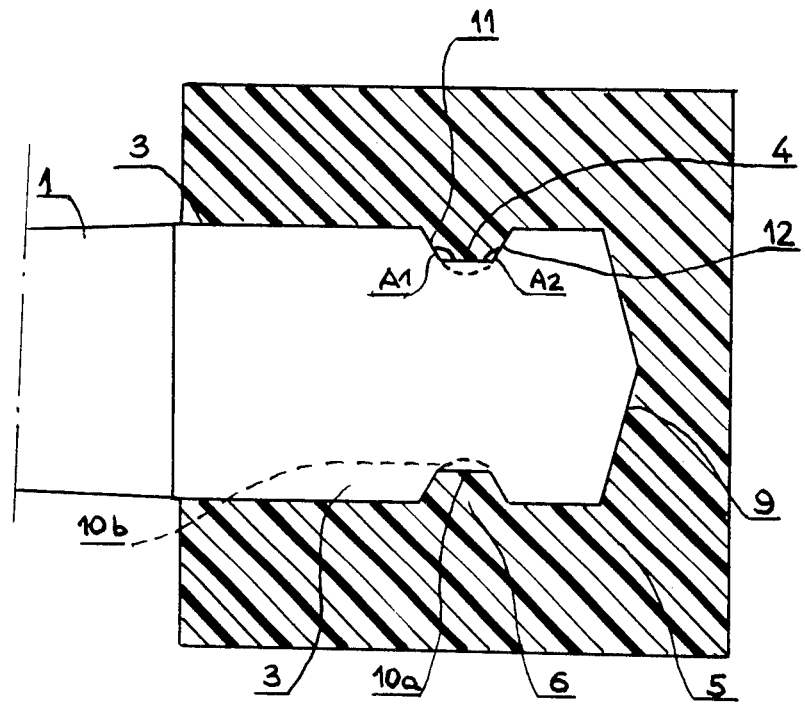
FIG. 12 is a close-up sectional view of the head of the post showing, in particular, the bottom of the groove and the angles of the sides of said groove.

The shape of the groove (4) may vary, depending on the technical characteristics of the impression compound (5) employed; thus, the bottom (10) of the groove (4) may be either flat (10a) or U-shaped [in cross section] (10b) (see FIG. 12). Moreover, the sides (11) and (12) of the groove (4) can form with said bottom (10) (10a or 10b) an angle A1 and an angle A2 that can vary from 90° to over 130°. Angles A1 and A2 of the sides (11) and (12) need not be identical: the side (12) which is nearest to the top (9) of the head (3) can form an angle different from that formed by side (11) which is nearest to the intraradicular tip (2) of the post (1).

I claim:

1. The combination of a radicular post and a resilient dental impression for use in preparing a cap to be fixed to a tooth having a post hole shaped to receive the post, the post comprising a conical part for entering the post hole, the post having a cylindrical part which extends from the tooth when the post is seated in the post hole and the cylindrical part having retention groove means circularly disposed around it, and the conical part and the cylindrical part and the groove means being fully symmetrically disposed about the longitudinal axis of the post; and the impression comprising a cured resilient compound having a molded hole fitting the cylindrical part of the post, and the impression having resilient ring means in the molded hole shaped to enter and fill the groove means in the post, the shape of the groove means and the resilience of the impression being selected such that the cylindrical part of the post can be removed from and re-positioned within the molded hole in the impression without damaging the impression and while achieving accurate positioning of the post therein because the parts of the post are symmetrical about said longitudinal axis.

2. The method of preparing a dental impression for making a cap to be fixed to a tooth having a post hole shaped to receive a radicular post, comprising the steps of:

installing and seating a post in the post hole, the post having a conical part for entering the post hole and having a cylindrical part to project from the tooth, and the cylindrical part having retention groove means circularly disposed around it, and the conical and cylindrical parts being symmetrically disposed about the longitudinal axis of the post;

molding resilient impression compound over the tooth and the projecting part of the post leaving no voids, whereby to form an impression having an internal hole fitting said cylindrical part of the post and having ring means in the internal hole fitting the groove means; and removing the molded impression and the post from the tooth, the shape of the groove means and the resilience of the ring means within the impression being selected to provide a reversible lock whereby in the event that the post remains in the tooth during removal of the impression a post which is identical in shape can be reinserted and locked in the internal hole and will be properly positioned therein during subsequent laboratory steps because the parts of the post are symmetrical about its longitudinal axis and thus have no specific orientation in terms of angle of rotation in the impression about said axis.

* * * * *